(12) United States Patent
Shah et al.

(10) Patent No.: US 8,685,639 B2
(45) Date of Patent: Apr. 1, 2014

(54) DIAGNOSIS AND PROGNOSIS OF WOUND INFECTION BY MEASUREMENT OF A PHOSPHOLIPASE $A_2$ IN WOUND FLUID

(75) Inventors: Faraia Shah, Bradford (GB); Rachael Clark, Skipton (GB); Patrick John Trotter, Leeds (GB); Paul William Watt, Steeton (GB); Breda Mary Cullen, Skipton (GB)

(73) Assignee: Woundcheck Laboratories (US), Inc., Quincy, MA (US)

( * ) Notice: Subject to any disclaimer, the term of this patent is extended or adjusted under 35 U.S.C. 154(b) by 1713 days.

(21) Appl. No.: 11/608,940

(22) PCT Filed: Jun. 9, 2005

(86) PCT No.: PCT/GB2005/002262
§ 371 (c)(1),
(2), (4) Date: Dec. 11, 2006

(87) PCT Pub. No.: WO2005/121357
PCT Pub. Date: Dec. 22, 2005

(65) Prior Publication Data
US 2007/0231380 A1    Oct. 4, 2007

Related U.S. Application Data

(60) Provisional application No. 60/625,830, filed on Nov. 8, 2004.

(30) Foreign Application Priority Data

Jun. 11, 2004 (GB) .................................. 0413078.7

(51) Int. Cl.
*C12Q 1/00* (2006.01)
(52) U.S. Cl.
USPC .......................................................... 435/4

(58) Field of Classification Search
USPC ................................................................ 435/4
See application file for complete search history.

(56) References Cited

U.S. PATENT DOCUMENTS 5,266,266 A    11/1993    Nason

FOREIGN PATENT DOCUMENTS

| WO | WO 9505479 A | 2/1995 |
|---|---|---|
| WO | WO 0054052 A | 9/2000 |
| WO | WO 03040406 A | 5/2003 |
| WO | WO 03101487 A1 | 12/2003 |

OTHER PUBLICATIONS

Sirois et al. "Biochemical components of bronchoalveolar lavage in early experimental asbestosis of the sheep: phospholipase A2 activity, prostaglandin E2 and proteins", Environmental Health Perspectives, 1983, 51:293-298.*
Kim et al. "Brochoaleolar lavage fluid phospholipase A2 activities are increased in human adult respiratory distress syndrome", Am. J. Physiol., 1995, 269(13):L109-L118.*
Zachary et al. "Signaling transduction mechanisms mediating biological actions of the vascular endothelial growth factor family", Cardiovascular Research, 2001, 49:568-581.*
Hamoon, A. N. et al., "Production of Extracellular Virulence Factors by *Pseudomonas aeruginosa* Isolates Obtained from Tracheal, Urinary Tract, and Wound Infections", J. of Surgical Researches 61, 425-432 (1996).

* cited by examiner

*Primary Examiner* — Bin Shen
(74) *Attorney, Agent, or Firm* — Brian B. Shaw, Esq.; Andrew J. Anderson, Esq.; Harter Secrest & Emery LLP

(57) ABSTRACT

The present invention relates to the diagnosis, prognosis and/or treatment of wound infection by testing wound fluid for the presence of a marker which is present in an amount which is indicative of infection. The marker may be high molecular weight phospholipase $A_2$ (cPLA$_2$) or a marker which is correlated with cPLA$_2$.

12 Claims, 1 Drawing Sheet

DIAGNOSIS AND PROGNOSIS OF WOUND INFECTION BY MEASUREMENT OF A PHOSPHOLIPASE $A_2$ IN WOUND FLUID

CROSS-REFERENCE TO RELATED APPLICATIONS

This application, which is the national stage of international application PCT/GB2005/002262 that was filed Jun. 9, 2005, claims priority to, and the benefit of, GB0413078.7 that was filed Jun. 11, 2004 and benefit of U.S. Provisional Application No. 60/625,830 that was filed Nov. 8, 2004.

All documents cited herein are incorporated by reference in their entirety.

TECHNICAL FIELD

The present invention relates to the diagnosis and prognosis of inflammatory conditions, in particular wound infection, by testing wound fluid for the presence of a marker which is present in an amount which is indicative of an inflammatory condition. The marker may be high molecular weight phospholipase $A_2$ ($cPLA_2$) or a marker indicative of the presence of $cPLA_2$.

The present invention provides methods of diagnosis and prognosis, methods of treatment, diagnostic devices (e.g. biosensors) and kits for use in such methods.

BACKGROUND ART

In mammals, injury triggers an organized complex cascade of cellular and biochemical events that result in a healed wound. Wound healing is a complex dynamic process that results in the restoration of anatomic continuity and function; an ideally healed wound is one that has returned to normal anatomic structure, function and appearance.

Chronically contaminated wounds all contain a tissue bacterial flora. These bacteria may be indigenous to the patient or might be exogenous to the wound. Closure, or eventual healing of the wound is often based on a physician's ability to control the level of this bacterial flora. Infection of wounds by bacteria delays the healing process, since bacteria compete for nutrients and oxygen with macrophages and fibroblasts, whose activity are essential for the healing of the wound. Infection results when bacteria achieve dominance over the systemic and local factors of host resistance. Infection is therefore a manifestation of a disturbed host/bacteria equilibrium in favour of the invading bacteria. This elicits a systemic septic response, and also inhibits the multiple processes involved in wound healing. Lastly, infection can result in a prolonged inflammatory phase and thus slow healing, or may cause further necrosis of the wound. The granulation phase of the healing process will begin only after the infection has subsided.

In clinical practice, a diagnosis of infection is based on the presence of local pain, heat, swelling, discharge and redness, although many clinical indicators, such as inflammation and discharge, have a low predictive value of infection in wounds. Definitive diagnosis is achieved by microbiological analysis of wound samples. Tissue biopsy provides the most accurate results, but this is an invasive procedure that is difficult to achieve for the mass of specimens required. Wound swabbing is the most common wound sampling method used in the UK although its clinical value has been questioned. Furthermore, microbiological diagnosis of wound infection can take 48 to 72 hours, which allows time for infection to further develop if first-line/best-guess treatment is not employed immediately.

There therefore remains a need in the art for a method for the early diagnosis and prognosis of wound infection, and for devices and wound dressings for use in carrying out such methods.

$cPLA_2$ are enzymes that hydrolyse the sn-2 position of membrane glycerophospholipids to liberate arachidonic acid. The activity of these enzymes is therefore important in the production of eicosanoids (e.g. prostaglandins and leukoriennes) and therefore associated with inflammation and host defence mechanisms. A detailed review can be found in Kudo and Murakami, Prostaglandins and other Lipid Mediators (2002) 68-69, 3-58.

There are essentially two groups of $PLA_2$: high molecular weight $PLA_2$ (cytosolic $PLA_2$) and low molecular weight $PLA_2$ (soluble $PLA_2$). High Mol. Wt. cytosolic $cPLA_2$ is normally located intracellularly and as such would not be expected to be present in wound fluid. There are three isoforms of this $cPLA_2$: $\alpha$ (110 kda), $\beta$ (85 kDa) and $\gamma$ (60 kDa) (See Kudo and Murakami, 2002). The low molecular weight soluble $PLA_2$'s ($sPLA_2$) are known to act intracellularly and, in contrast to $cPLA_2$, we have not found any evidence that the low molecular weight form ($sPLA_2$) is elevated in infected wound fluid.

WO03/101487 describes a method of assessing neural inflammatory disease in an animal by determining the level of phospholipase $A_2$ protein (including $cPLA_2$) in tissue or body fluid such as blood, plasma and cerebrospinal fluid. It does not appear to teach or suggest the association of $cPLA_2$ with extracellular wound fluid or as a marker of bacterial infection.

WO00/54052 describes an assay for detecting $cPLA_2$ in or on red blood cells, in particular for the diagnosis of diseases in which dysfunction of cell signalling systems involving highly unsaturated fatty acids are implicated. This reference does not appear to teach or suggest the testing of extracellular fluid for the presence of $cPLA_2$ to diagnose infection of a wound.

Funakoshi et al. in *Pancreas* (1991) vol. 6(5), pp 588-594 disclose that serum $PLA_2$ levels are elevated in the sera of patients with pancreatic diseases and that the measurement of serum $PLA_2$ is useful for diagnosis and monitoring of pancreatitis. There is no teaching or suggestion any association of $cPLA_2$ with extracellular wound fluid or as a marker of bacterial infection.

DISCLOSURE OF THE INVENTION

The present invention relates to a marker of inflammation/infection that could be used as a target molecule in a new diagnostic/prognostic assay (e.g. laboratory based or point of care) to identify an inflammatory condition such as infection. The marker may be high molecular weight phospholipase $A_2$ ($cPLA_2$) or a marker which is correlated with $cPLA_2$.

Western blot analysis of wound fluid from infected and non-infected patients shows that $cPLA_2$ and $cPLA_2$ fragments (three bands are present) are observed in infected wound fluid (IV13) and no immunoreactivity to cPLA or $cPLA_2$ fragments was seen in the non-infected wound fluid (see attached FIG. 1). Based on the specificity of the antibody and the molecular weight it is believed that the three bands observed correspond to $cPLA_2\alpha$ (110 kda), $cPLA_2\beta$ (85 kDa) and $cPLA_2\gamma$ (60 kDA).

$cPLA_2$ normally acts intracellularly and is not normally present in an wound environment. The observation that isoforms of this protein are present in infected but not in non-infected wound fluid is therefore novel and surprising. It is believed that the data presented herein represents the first demonstration that the cytosolic form of $PLA_2$ is even present in wound fluid.

The finding that $cPLA_2$ is present in infected fluid means that the differentiation between infected and basal levels is significant. $cPLA_2$ (and fragments thereof) could therefore be used as a marker of inflammatory conditions such as infection and components for detecting or measuring the same could be incorporated in any type of diagnostic/prognostic kit (lab based (e.g. ELISA) or point of care (e.g. an antibody type kit similar to commercially available pregnancy kits). Further, $cPLA_2$ and $cPLA_2$ fragments may not only serve as markers of wound infection but may be useful as general host derived markers of infection. Similarly, markers indicative of the presence of $cPLA_2$ may be used.

A first aspect of the invention provides a method of diagnosing or prognosing wound infection, the method comprising testing wound fluid for the presence or level of $cPLA_2$ or a marker which is indicative of the presence or level of $cPLA_2$ in wound fluid.

A second aspect of the invention provides a diagnostic device selected from the group consisting of wound dressings and biosensors for use in diagnosing or prognosing wound infection, comprising components of an assay system for testing wound fluid for the presence or level of $cPLA_2$ or a marker which is indicative of the presence or level of $cPLA_2$ in wound fluid.

A further aspect of the invention provides a diagnostic or prognostic kit for the diagnosis or prognosis of wound infection, the kit comprising a wound dressing or biosensor according to the second aspect of the invention.

A further aspect of the invention relates to the use of components of an assay system for identifying in wound fluid the presence or level of: (i) $cPLA_2$; or (ii) a marker indicative of the presence or level of $cPLA_2$ in wound fluid, in the manufacture of a biosensor, wound dressing, diagnostic or prognostic kit for diagnosing or prognosing wound infection in a patient.

A further aspect of the invention relates to a system for use in the diagnosis and treatment of wounds comprising a diagnostic device according to the invention, and a wound dressing comprising at least one antimicrobial agent for application to the wound when the measured presence or level of $cPLA_2$ or of a marker which is indicative of the presence or level of $cPLA_2$ is indicative of wound infection.

A further aspect of the invention relates to a method for the treatment of a mammalian wound comprising the steps of measuring the presence or level of $cPLA_2$ or a marker which is indicative of the presence or level of $cPLA_2$, in a wound fluid collected from the wound, and applying an antimicrobial wound dressing to the wound selectively if the said presence or level is indicative of wound infection.

Whilst the invention has been described in relation to $cPLA_2$ it is envisaged that other lipases may find utility as markers of infection.

Testing the Wound Fluid

The test on the wound fluid may be qualitative. Alternatively, a quantitative or semi-quantitative test for the marker (i.e. $cPLA_2$ or a marker indicative of the presence or level of $cPLA_2$) may be performed. Thus, in one embodiment the concentration of the marker is measured.

In one embodiment, the method is performed on wound fluid or serum which has been removed from body (e.g. as a clinical swab or as a fluid sample). In another embodiment, the method is performed on would fluid in situ. For example, the wound fluid may be tested by means of an implanted device or dressing attached to patient. The decision as to which method is used will depend upon the type of wound in question.

Various methods may be used to detect or measure the concentration of the marker. Suitable methods include those utilizing chemical or enzyme-linked reactions, or immunological (e.g. ELISA, western blots), spectrophotometric, colorimetric, fluorimetric, or radioactive detection based techniques. In one embodiment a dip-stick type test is provided. Such a test could be used in the community and by the patient allowing easier and earlier diagnosis/prognosis.

For example, in the case of surface-exposed wounds, a clinical swab, dressing, "dipstick" or other biosensor device may be applied directly to the surface of the wound. The device should contain the components of the assay system for detecting the marker so that the assay reaction may itself proceed in situ. The device can then be removed from the wound and the signal measured by the appropriate means. In many cases, a physician may not actually require an accurate assessment of the precise concentration of the marker, but may just wish to know whether there is a sufficient concentration of the marker to warrant prophylactic or curative action as necessary. In these cases, visible assessment of the dressing may be sufficient to allow identification of the specific areas of infection. Unnecessary treatment of healthy granulating tissue can then be avoided.

A dressing that allows mapping of the infected areas of a wound will be preferable in certain instances. Diagnostic wound mapping sheets that could be adapted to the methods of the present invention are described in GB-A-2323166 (application no. GB 9705081.9), filed on 12th Mar. 1997, the entire content of which is hereby incorporated by reference.

Immobilization of reaction components onto a dipstick, wound mapping sheet or other solid or gel substrate offers the opportunity of performing a more quantitative measurement. For example, in the case of a reaction linked to the generation of a colour the device may be transferred to a spectrometer. Suitable methods of analysis will be apparent to those of skill in the art.

Immobilization of the reaction components to a small biosensor device will also have the advantage that less of the components (such as antibody, enzyme and substrate) are needed. The device will thus be less expensive to manufacture than a dressing that needs to have a large surface area in order to allow the mapping of a large wound area.

Methods for the incorporation of the components of the assay reaction onto a clinical dressing, "dipstick" sheet or other biosensor are routine in the art. See for example Fägerstam and Karlsson (1994) *Immunochemistry,* 949-970.

Suitably, the methods, uses and/or devices, of the present invention comprise an immunological binding partner for the $cPLA_2$ or for the marker which is indicative of the presence or level of $cPLA_2$. Suitable immunological binding partners include antibodies, including both polyclonal antibodies and monoclonal antibodies. Antibodies which may be employed in the present invention include Polyclonal antibody against c-terminal end of PLA2(abcam 9014); and monoclonal antibody to cPLA2-US Biological Cat non. P4074-04 and are available commercially. The immunological binding partner may be immobilized or bound to a solid substrate in a device as described herein.

The detectable signal produced by the device according to the present invention is observable or measurable by a physical, chemical, or biological means known to those of skill in the art. A detectable signal may be a change in emission or absorbance of electromagnetic waves at a certain wavelength, hybridization or enzymatic reaction. In preferred embodiments, detectable signals are changes in colour when viewed under white light or fluorescence when viewed under UV light. In certain embodiments, the device may comprise an electronic sensor, for example to detect color change or fluorescence and to provide a quantitative output thereof The device may include an electronic sensor that can provide a quantitative output in digital form.

The device may further comprise a reference assay element for determining the total protein content of the sample, so that the measured level of $cPLA_2$ or of a marker which is indicative of the presence or level of $cPLA_2$, can be normalised to constant total protein level in order to increase accuracy.

In certain embodiments, the device according to the present invention comprises, or consists essentially of a wound dressing, dipstick or swab. In certain embodiments, the device according to the present invention comprises a housing containing one or more reagents and having an inlet provided therein for introduction of the sample. The housing may be at least partially transparent, or may have windows provided therein, for observation of an indicator region that undergoes a color or fluorescence change. In certain embodiments, the device operates on the lateral flow principle. That is to say, said device comprises a housing having an inlet for the sample and side walls defining a fluid lateral flow path extending from the inlet. By "lateral flow", it is meant liquid flow in which the dissolved or dispersed components of the sample are carried, preferably at substantially equal rates, and with relatively unimpaired flow, laterally through the carrier. Suitably, the fluid flow path contains one or more porous carrier materials. The porous carrier materials are preferably in fluid communication along substantially the whole fluid flow path so as to assist transfer of fluid along the path by capillary action. Suitably, the porous carrier materials are hydrophilic, but preferably they do not themselves absorb water. The porous carrier materials may function as solid substrates for attachment of reagents or indicator moieties In certain embodiments of the present invention, the device further comprises a control moiety located in a control zone in said in said device, wherein the control moiety can interact with a component of the wound fluid sample to improve the accuracy of the device.

The size and shape of the carrier are not critical and may vary. The carrier defines a lateral flow path. Suitably, the porous carrier is in the form of one or more elongate strips or columns. In certain embodiments, the porous carrier is one or more elongate strips of sheet material, or a plurality of sheets making up in combination an elongate strip. One or more reaction zones and detection zones would then normally be spaced apart along the long axis of the strip. However, in some embodiments the porous carrier could, for example be in other sheet forms, such as a disk. In these cases the reaction zones and detection zones would normally be arranged concentrically around the center of the sheet, with a sample application zone in the center of the sheet. In yet other embodiments, the carrier is formed of carrier beads, for example beads made from any of the materials described above. The beads may suitably be sized from about 1 micrometer to about 1 mm. The beads may be packed into the flow path inside the housing, or may be captured or supported on a suitable porous substrate such as a glass fiber pad.

It will be appreciated that the devices according to the present invention may be adapted to detect at least one analyte in addition to the $cPLA_2$ or the marker which is indicative of the presence or level of $cPLA_2$. This can be done by the use of several different reagents in a single reaction zone, or preferably by the provision in a single device of a plurality of lateral flow paths each adapted for detecting a different analyte. In certain embodiments, the plurality of lateral flow paths are defined as separate fluid flow paths in the housing, for example the plurality of lateral flow paths may be radially distributed around a sample receiving port. In some embodiments, the plurality of fluid flow paths are physically separated by the housing. In other embodiments multiple lateral flow paths (lanes) can be defined in a single lateral flow membrane by depositing lines of wax or similar hydrophobic material between the lanes.

The devices according to the present invention may for example be incorporated into a bacterial sensing device of the kind described in copending application GB 0501818.9 filed on 28th Jan. 2005, the entire content of which is incorporated herein by reference.

Briefly, the devices of GB 0501818.9 are lateral flow sensors for the detection of endogenous and/or microbial protease enzymes in wound fluid in order to ascertain the amount and type of bacterial infection. The devices comprise: a housing having an inlet for the sample and side walls defining a fluid flow path extending from the inlet, an indicator moiety that is bound to a solid substrate by means of a peptide linker moiety that is cleavable by the analyte enzyme, the solid substrate being located in a reaction zone of the fluid flow path; and a detector moiety located in a detection zone downstream from the reaction zone in the fluid flow path, wherein the detector moiety can interact with an indicator moiety that has been cleaved from the solid substrate to produce a detectable change in the detection zone.

An absorbent element may suitably be included in the devices of the present invention. The absorbent element is a means for drawing the whole sample through the device by capillary attraction. Generally, the absorbent element will consist of a hydrophilic absorbent material such as a woven or nonwoven textile material, a filter paper or a glass fiber filter The device may further comprise at least one filtration element to remove impurities from the sample before the sample undergoes analysis. The filtration device may for example comprise a microporous filtration sheet for removal of cells and other particulate debris from the sample. The filtration device is typically provided upstream of the sample application zone of the fluid flow path, for example in the inlet of the housing or in the housing upstream of the inlet.

Preferably, the devices according to the present invention include a control moiety in a control zone of the device, wherein the control moiety can interact with a component of the wound fluid sample to improve the accuracy of the device. Suitably, the control zone is adapted to reduce false positive or false negative results. A false negative result could arise for various reasons, including (1) the sample is too dilute, or (2) the sample was too small to start with.

In order to address false negative mechanism , the control zone preferably further comprises a reference assay element for determining the total protease content or the total protein content of the sample, that is to say for establishing that the total protease content or the total protein content of the sample is higher than a predetermined minimum. It is possible to indicate the presence of protein by the use of tetrabromophenol blue, which changes from colorless to blue depending on the concentration of protein present. It is also possible to detect glucose (using glucose oxidase), blood (using diisopropyl-benzene dihydro peroxide and tetramethylbenzidine), leukocytes (using ester and diazonium salt). These may all be useful analytes for detection in the control zone for the reduction of false negatives.

In a further aspect, the present invention provides a diagnostic test system or kit comprising a diagnostic device according to the present invention. The test system or kit may comprise, in addition to a diagnostic device according to the present invention, one or more components selected from: a color chart for interpreting the output of the diagnostic device, a sampling device for collecting a sample of a wound fluid from a wound, a wash liquid for carrying a sample of wound fluid through the device, and a pretreatment solution containing a reagent for pretreatment of the wound fluid sample.

Where present, the sampling device may comprise a swab or a biopsy punch, for example a shaft having a swab or biopsy punch attached thereto. Suitably, the diagnostic device includes a sample receiving port, and preferably the sample receiving port and the swab or biopsy punch comprise complementary fitting elements whereby the swab or biopsy punch can be secured to the device with the swab or biopsy punch received in the sample receiving port.

In certain embodiments the fitting element on the shaft may be located from 1 mm to about 30 mm from the base of the swab or the biopsy punch. This is consistent with the use of relatively small sample receiving port on the housing of the diagnostic device. The sample receiving port is typically located on an upper surface of the diagnostic device, and it is typically generally in the form of an upwardly projecting tube, open at the top and having the inlet to the fluid flow path located at the bottom of the tube. Suitable swabs, biopsy punches and sample receiving caps are described in detail in copending applications GB0403976.4 and GB0403978.0 both filed on 23rd Feb. 2004, the entire contents of which are incorporated herein by reference.

The fitting element on the shaft may a tapered region of the shaft for forming an interference fit with the housing, for example it may appear as a truncated cone that is coaxial with the shaft and tapers towards the first end of the shaft. Or the whole shaft may have a diameter larger than that of the swab or biopsy punch, with a tapered region adjacent to the first end. In any case, the diameter of the tapered region where it engages with the housing is normally greater than the diameter of the swab or biopsy punch, so that the inlet port can enclose the swab or biopsy punch.

In other embodiments, the engagement element may comprise a snap-fitting projection for forming a snap-fit with one or more complementary projections on an inner surface of the housing, or a threaded projection for forming a screw fit with one or more complementary threads on an inner surface of the cap, or a Luer-lock type fitting.

The swab may be any absorbent swab, for example a nonwoven fibrous swab. Typically the diameter of the swab is about 2 to about 5 mm, for example about 3 mm. In certain embodiments, the swab may be formed from a medically acceptable open-celled foam, for example a polyurethane foam, since such foams have high absorbency and can readily be squeezed to expel absorbed fluids. The biopsy punch will typically be a stainless steel cylindrical punch of diameter about 1 mm to about 10 mm, for example about 3 mm to about 8 mm, suitably about 6 mm.

In certain embodiments the shaft is hollow, whereby a fluid can be passed down the shaft from the second end to expel the biological sample from the swab or the biopsy punch into the diagnostic device. This helps to ensure that all of the sample passes through the device, thereby avoiding false negatives. The shaft may comprise a fitting at the second end for attachment of a syringe or other source of the fluid. In certain embodiments, the apparatus may comprise a reservoir of liquid attached to the second end of the shaft, for example a compressible bulb containing the liquid, which can be activated after use of the swab or biopsy punch. Suitable devices of this kind are described, for example in U.S. Pat. No. 5,266,266, the entire content of which is incorporated herein by reference. In other embodiments, the apparatus may comprise a plunger that can be pushed down the hollow bore of the shaft to expel fluid or other specimens from the swab or biopsy punch.

Another advantage of the hollow shaft is that, where the apparatus is a biopsy punch, the biopsy sample can more readily be pushed or blown out of the punch. The biopsy punch apparatus can further comprise a homogenizing tool that can be passed down the hollow shaft to homogenize a tissue sample in the biopsy punch. This step of homogenizing can be followed, if necessary, by passing liquid down the shaft from the second end to expel the homogenized tissue from the biopsy punch into the device for diagnostic analysis.

In this aspect of the invention, the swab or biopsy punch may be sterilized, and may be packaged in a microorganism-impermeable container. The diagnostic devices according to the present invention may also be sterilized, but they may not, because the devices often do not come into contact with the patient being diagnosed.

The concentration of the marker may also be measured in an aqueous assay system. For instance, wound fluid may be extracted directly from the environment of the wound or can be washed off the wound using a saline buffer. The resulting solution can then be assayed for the concentration of the marker in, for example, a test tube or in a microassay plate.

Such a method will be preferable for use in cases in which the wound is too small or too inaccessible to allow access of a diagnostic/prognostic device such as a dipstick. This method has the additional advantage that the wound exudate sample may be diluted.

It will be clear that an aqueous assay system is more applicable to use in a laboratory environment, whereas a wound dressing containing the necessary reaction components will be more suitable for use in a hospital or domestic environment.

The presence or level of a single or plurality (e.g. 2, 3, 4, 5 or more) of markers as defined in claim 1 may be assayed in the methods and devices of the invention.

In a further aspect of the invention, there is provided a method of determining whether a wound is infected, the method comprising testing would fluid from the wound for the presence or level of $cPLA_2$ or a marker indicative of the presence or level of high molecular weight $cPLA_2$. Preferably, the method comprises the steps of contacting the indicator device of the invention with a sample, and assessing the generation of a detectable signal from the indicator device.

In certain embodiments according to this aspect, the method is adapted to determine whether the presence or level of $cPLA_2$ or a marker indicative of the presence or level of high molecular weight $cPLA_2$ in a sample of wound fluid exceeds a predetermined minimum level which is characteristic of an infection. In other embodiments, method is adapted to determine whether the presence or level of $cPLA_2$ or a marker indicative of the presence or level of high molecular weight $cPLA_2$ in a sample of wound fluid exhibits an increase over time that is indicative of the development of infection.

In a further aspect, the present invention provides a method for the treatment of a wound comprising the steps of measuring the presence or level of $cPLA_2$ or a marker indicative of the presence or level of high molecular weight $cPLA_2$ of a wound fluid collected from the wound, and applying an antimicrobial wound dressing to the wound selectively if the said presence or level is indicative of wound infection. Preferably, the method further comprises applying a wound dressing that is substantially free of antimicrobial agents to the wound if the said presence or level of $cPLA_2$ or a marker indicative of the presence or level of high molecular weight $cPLA_2$ is indicative of absence of wound infection.

Preferably, the method according to this aspect comprises sampling the wound fluid at intervals, for example at intervals of from 1 hour to 24 hours, and selecting an antimicrobial or non-antimicrobial dressing to treat the wound at said intervals in response to the presence or level of $cPLA_2$ or a marker indicative of the presence or level of high molecular weight $cPLA_2$. In certain embodiments, the wound dressing selection is determined by the cPLA2, whereby an antimicrobial dressing is applied when an increase in cPLA2 is detected, and a conventional non-antimicrobial dressing is applied if the cPLA2 is constant or falling.

Preferably, the method her comprises determining the total protein content of the sample, whereby the presence or level of $cPLA_2$ or a marker indicative of the presence or level of high molecular weight $cPLA_2$ can be normalised to constant total protein content.

In a further aspect, the invention also provides a system for use in the diagnosis and treatment of wounds comprising a diagnostic device according to the invention and a wound dressing comprising at least one antimicrobial agent The wound dressing comprising the antimicrobial agent(s) can be applied to the wound selectively, when the diagnostic device indicates the presence of wound infection.

Preferably, the system according to this aspect further comprises a wound dressing that is substantially free from antimicrobial agents, for application to the wound when the measured presence or level of $cPLA_2$ or a marker indicative of the presence or level of high molecular weight $cPLA_2$ is indicative of a non-infected wound. The system may be in the form of a kit, and the device and the wound dressing(s) may be packaged together in a single package.

These aspects of the invention avoid unnecessary application of antimicrobial agents to the wound, which is desirable because most antimicrobial agents are cytotoxic and interfere with wound healing, and also to avoid the development of resistant microorganisms.

The antimicrobial wound dressing used in these aspects of the invention comprises an effective amount of an antimicrobial agent, which may preferably be selected from the group consisting of antiseptics and antibiotics and mixtures thereof Suitable antibiotics include peptide antimicrobials (e.g. defensins, Magainin, synthetic derivatives of them) tetracycline, penicillins, terramycins, erythromycin, bacitracin, neomycin, polymycin B, mupirocin, clindarnycin and mixtures thereof. Suitable antiseptics include silver sulfadiazine, chlorhexidine, povidone iodine, triclosan, other silver salts and colloidal silver, sucralfate, quaternary ammonium salts and mixtures thereof.

The wound dressing materials used in these aspects of the invention may for example be provided in the form of beads, flakes, powder, and preferably in the form of a film, a fibrous pad, a web, a woven or non-woven fabric, a freeze-dried sponge, a foam or combinations thereof. In certain embodiments, the dressing material is selected from the group consisting of woven fabrics, knitted fabrics, and nonwoven fabrics, all of which may be made by conventional methods. In other embodiments, the material may comprise (or consist essentially of) a freeze-dried sponge or a solvent-dried sponge The wound dressing material may be in the form of a solid, or a semi-solid ointment or gel. Preferably, the wound dressing material comprises only up to 20% by weight, preferably less than 10% by weight of water. The relatively low water content improves the stability of the material and makes it possible to sterilize by heat or irradiation without loss of activity. The material may also contain 0-40% by weight, preferably 0-25% by weight of a plasticiser, preferably a polyhydric alcohol such as glycerol All of the above percentages are on a dry weight basis.

Any type of wound may be diagnosed or treated using the methods, apparatus and uses of the present invention. For example, the wound may be an acute wound such as an acute traumatic laceration, perhaps resulting from an intentional operative incision. More usually the wound may be a chronic wound. Preferably, the chronic wound is selected from the group consisting of venous ulcers, pressure sores, decubitis ulcers, diabetic ulcers and chronic ulcers of unknown aetiology. The present invention may be used in the diagnosis or prognosis of human and non-human mammalian animals.

As used herein, the term wound fluid is meant to refer to the exudate that is secreted or discharged by cells in the environment of the wound. The term "wound fluid" herein refers to any wound exudate or other fluid preferably substantially not including blood) that is present at the surface of the wound, or that is removed from the wound surface by aspiration, absorption or washing. The term "wound fluid" does not normally refer to blood or tissue plasma remote from the wound site.

By testing wound fluid for the presence or level of $cPLA_2$, we include testing for $cPLA_2\alpha$, $cPLA_2\beta$ or $cPLA_2\gamma$.

As an alternative to testing for $cPLA_2$ directly, a marker which is indicative of the presence or level of $cPLA_2$ may be detected or measured. For instance, binding proteins which specifically bind with $cPLA_2$ may be suitable markers of inflammatory conditions. Examples include ERK1/2, P38 MAP kinase, S100 proteins, GTP binding proteins, annexins and calmodulin.

In addition as $cPLA_2$ acts on lipids other lipid binding proteins could be assayed such as prostaglandins, (e.g. PGE1) or fatty acid.

The skilled person will be able to verify the suitability of a particular cytosolic $PLA_2$ binding protein or lipid binding protein as a marker of an inflammatory condition by experimentally verifying that the level of the marker in wound fluid (e.g. wound fluid) from healthy patients statistically differs from basal/normal levels of the marker and is thereby indicative of an inflammatory condition. Preferably, the marker is only present in negligible amounts (if at all) in the wound fluid of healthy patients.

The level of the marker is significantly different than the control (normal level) if the level of the marker differs from that of the control level by an amount greater than the standard error of the assay employed, and preferably at least twice, and more preferably three, four, five or ten times that amount. Alternately, the level of the marker can be considered "significantly" different than the control level of the marker if the marker level is at least about 1.5, two, three, four, or five times, higher or lower, respectively, than the control level of the marker.

MODES FOR CARRYING OUT THE INVENTION

EXAMPLE 1

Figure 1:
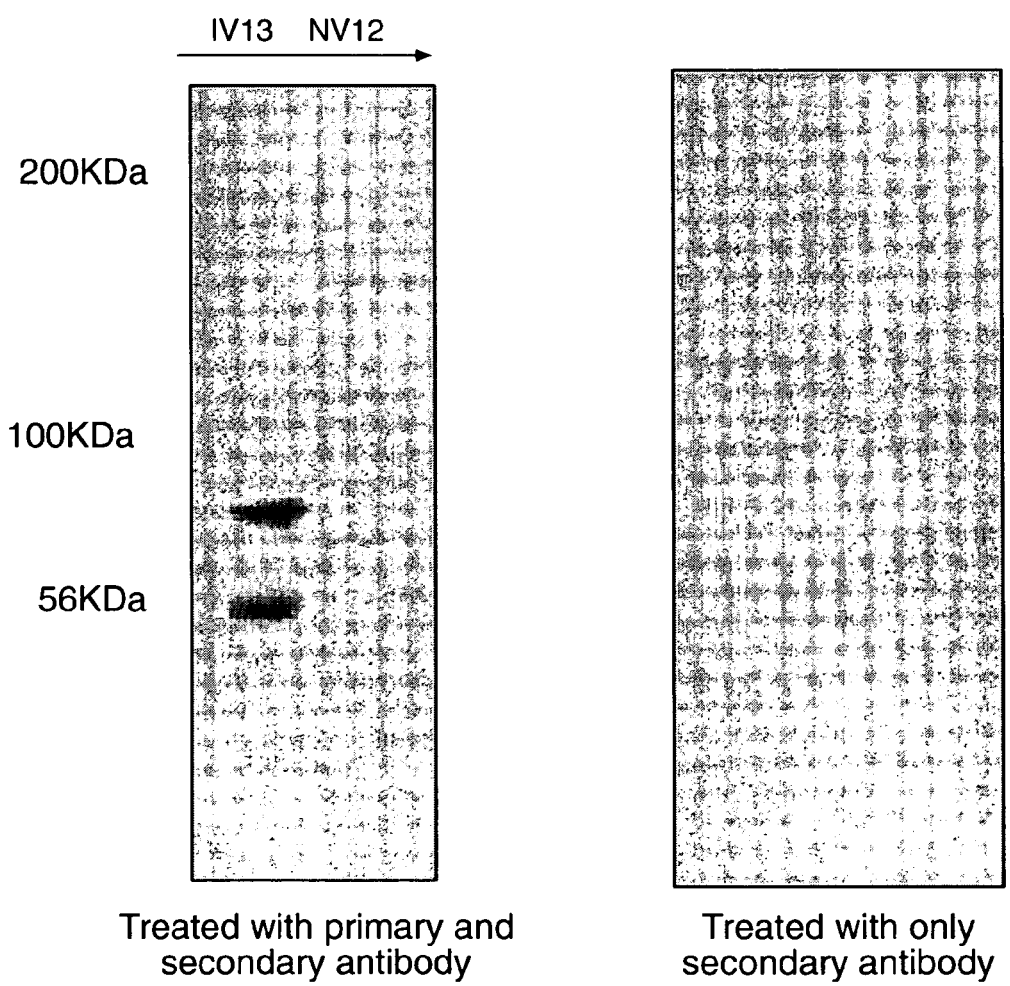
FIG. 1 shows the results of a Western blot for $cPLA_2$ in infected and non-infected wound fluid. NV and IV fluid diluted 1:10.

Collection and Treatment of Wound Fluid—Removal of Infected and Non-Infected Wound Fluid All patients enrolled in the study had venous leg ulcers of at least 30 days duration and a surface area of at least 1 cm². Patients were diagnosed as 'non-infected', normal appearance of wound, or 'infected' based on a minimum of 4 clinical signs and symptoms indicative of infection. Patients were excluded from the study if exposed bone with positive osteomyelitis was observed. Other exclusion criteria included concomitant conditions or treatments that may have interfered with wound healing and a history of non-compliance that would make it unlikely that a patient would complete the study. Wound fluids were collected from the patients following informed consent being given from all patients or their authorized representatives The protocol was approved by the Ethics Committee at the participating study center prior to commencement of the study. The study was conducted in accordance with both the Declaration of Helsinki and Good Clinical Practice.

Sample Preparation

Total protein in each extracted wound fluid sample was determined using the Bradford protein assay, following manufacturers instructions for use of a Bio-Rad Protein Assay kit. All non-infected samples were then coded by NV followed by a specific number and the infected samples coded by IV followed by a number. Neat samples were diluted in PBS as 1:5 and 1:10 and then mixed by pipetting with reduced treatment buffer—20 ul wound fluid mixed with 5 ul reduced treatment buffer and then boiled for 5 mins in a water bath, to degrade proteins to fragments and produce reduced samples. (NB tops of the eppendorf tubes must be open). Following this treatment all samples were frozen in −20° C. until required for western blot analysis.

Western Blotting

Wound fluid from non-infected patient identified as NV12 and an infected patient IV13 was used. Broad range SDS page marker (Catalog number 161-0318 obtained from Biorad) was used as a standard and 10% Tris-HCl gels (Biorad) used. Samples were loaded in the gel and SDS page electrophoresis carried out at 60 mA until the samples ran to the bottom of the gel. Gels were transferred onto nitrocellulose paper of pore size 0.45 um (Biorad) at 200 mA over 3 hrs whilst immersed in ice. Following gel transfer, nitrocellulose paper was washed in PBS/0.1% Tween solution for 5 mins and then blocked in 5% milk for 1 hr at room temperature, RT, on shaker. Following another wash in PBS/Tween solution, one blot was treated with primary antibody (abeam one polyclonal antibody, abeam 9014) diluted in PBS/Tween solution and the second blot was treated with only PBS/Tween solution as a control. Both blots were left on the shaker overnight at RT. The polyclonal primary antibody was obtained from Autogen Bioclear UK (sc20105) at a concentration of 200 ug/ml and diluted −100 ul neat added to 9,900 ul PBS/Tween solution. Following incubation with the primary antibody, blots were washed every 5 mins in PBS/Tween solution for 30 mins and then treated to secondary antibody (anti-sheep HRP-linked antibody obtained from Sigma) for 1 hr at RT on the shaker. The blots were then developed using the Opti4 CN kit (Biorad) for 5-10 mins and the bands observed.

Additional Data

FIG. 1 shows information from one infected and one non infected patient. To confirm this observation the wound fluid of five non-infected (NV2, 5, 9, 12 and 14) and five infected patients (IV 1, 4, 10, 13 and 22) was assessed using the method as described above.

These results demonstrated that no cPLA$_2$ was observed in the non infected patients and cPLA$_2$ was present in 4 out of five infected patients. This additional experiment confirms that cPLA$_2$ is a marker of wound infection.

It will be understood that the invention has been described by way of example only and modifications may be made whilst remaining within the scope and spirit of the invention.

The invention claimed is:

1. A method of diagnosing or prognosing wound infection, comprising testing a wound fluid for the presence or level of high molecular weight phospholipase A$_2$ (cPLA$_2$) or of a marker which is indicative of the presence or level of cPLA$_2$, wherein the presence or level of said cPLA$_2$ or said marker is indicative of wound infection, wherein the wound is a chronic wound selected from the group consisting of a venous ulcer, a pressure sore, a decubitis ulcer, a diabetic ulcer and a chronic ulcer of unknown etiology.

2. The method, according to claim 1, wherein a concentration of cPLA$_2$ or the marker indicative of the presence or level of cPLA$_2$ is measured.

3. The method according to claim 1 wherein the method is performed on wound fluid in situ.

4. The method according to claim 1 wherein the method is an in vitro method that is performed on a sample of wound fluid that has been removed from a body.

5. A method for the treatment of a mammalian wound comprising the steps of measuring the presence or level of cPLA$_2$ or a marker which is indicative of the presence or level of cPLA$_2$ of a wound fluid collected from the wound, and applying an antimicrobial wound dressing to the wound selectively if the said presence or level is indicative of wound infection.

6. The method according to claim 5, further comprising applying a wound dressing that is substantially free of antimicrobial agents to the wound if the said presence or level is indicative of absence of wound infection.

7. The method according to claim 5, wherein the method comprises sampling the wound fluid at intervals, for example at intervals of from 1 hour to 24 hours, and selecting an antimicrobial or non-antimicrobial dressing to treat the wound at said intervals in response to the measured presence or level of cPLA$_2$ or a marker which is indicative of the presence or level of cPLA$_2$.

8. The method according to claim 7, wherein the antimicrobial wound dressing is applied to the wound if said level is increasing over time, and the non-antimicrobial dressing is applied to the wound if said level is decreasing over time.

9. The method according to claim 5, wherein wound fluid is tested for the presence or level of cPLA$_2$α, cPLA$_2$ β or cPLA$_2$γ.

10. The method, according to claim 5, wherein the marker which is indicative of the presence or level of high molecular weight cPLA2 is ERK½, P38 MAP kinase, a S100 protein, a GTP binding protein, an annexin, calmodulin, PGE1 or fatty acid synthase.

11. A method of diagnosing or prognosing wound infection, comprising testing a wound fluid for the presence or level of high molecular weight phospholipase A$_2$ (cPLA$_2$) or of a marker which is indicative of the presence or level of cPLA$_2$, wherein the presence or level of said cPLA$_2$ or said marker is indicative of wound infection, wherein the wound is an acute traumatic laceration.

12. A method of diagnosing or prognosing wound infection, comprising testing a wound fluid for the presence or level of high molecular weight phospholipase A$_2$ (cPLA$_2$) or of a marker which is indicative of the presence or level of cPLA$_2$, wherein the presence or level of said cPLA$_2$ or said marker is indicative of wound infection, wherein the wound is a surface-exposed wound.

* * * * *